US012631610B2

(12) United States Patent　　　　(10) Patent No.:　US 12,631,610 B2

Kaita et al.　　　　　　　　　　　(45) Date of Patent:　　May 19, 2026

(54) GAS SENSOR

(71) Applicant: TDK Corporation, Tokyo (JP)

(72) Inventors: Yoshio Kaita, Tokyo (JP); Hiroshi Kobayashi, Tokyo (JP); Yasuhiro Inui, Tokyo (JP)

(73) Assignee: TDK Corporation, Tokyo (JP)

( * ) Notice: Subject to any disclaimer, the term of this patent is extended or adjusted under 35 U.S.C. 154(b) by 279 days.

(21) Appl. No.: 18/486,297

(22) Filed: Oct. 13, 2023

(65) Prior Publication Data

US 2024/0151699 A1　　May 9, 2024

(30) Foreign Application Priority Data

Nov. 7, 2022　(JP) ................................. 2022-178048

(51) Int. Cl.
　　*G01N 33/00*　　　(2006.01)
　　*G01K 7/24*　　　　(2006.01)
　　*G01N 27/12*　　　(2006.01)
　　*G01N 27/18*　　　(2006.01)

(52) U.S. Cl.
　　CPC ............. *G01N 33/004* (2013.01); *G01K 7/24* (2013.01); *G01N 27/122* (2013.01); *G01N 27/123* (2013.01); *G01N 27/124* (2013.01); *G01N 27/18* (2013.01); *G01N 33/0073* (2013.01)

(58) Field of Classification Search
　　CPC ........ G01N 27/18; G01N 27/14; G01N 27/12; G01N 27/122; G01N 27/123; G01N 27/124; G01N 33/004; G01N 33/0073; G01K 7/24
　　See application file for complete search history.

(56) References Cited

U.S. PATENT DOCUMENTS

| | | | |
|---|---|---|---|
| 4,882,287 A | 11/1989 | Holter et al. | |
| 2003/0131653 A1 | 7/2003 | Bair, III et al. | |
| 2005/0066707 A1* | 3/2005 | Katsuki ............ | H01M 8/04089 73/25.03 |
| 2020/0088669 A1* | 3/2020 | König ............... | G01N 33/0062 |
| 2021/0003525 A1 | 1/2021 | Kaita et al. | |
| 2021/0132014 A1* | 5/2021 | Goel .................... | G01N 33/004 |

FOREIGN PATENT DOCUMENTS

| | | |
|---|---|---|
| JP | 51-140793 A | 12/1976 |
| JP | 58-11847 A | 1/1983 |
| JP | 58-158550 A | 9/1983 |
| JP | 2016-170161 A | 9/2016 |
| JP | 2019-060848 A | 4/2019 |

* cited by examiner

*Primary Examiner* — Paul M. West

(74) *Attorney, Agent, or Firm* — Rimon P.C.

(57) ABSTRACT

Disclosed herein is a gas sensor that includes a gas sensor part including first and second thermistors connected in series, a temperature sensor part configured to generate a temperature detection signal, a variable resistor connected in parallel to the first thermistor, and a control circuit configured to change a resistance value of the variable resistor based on the temperature detection signal.

11 Claims, 7 Drawing Sheets

| Table_No. | Environmental Temperature [°C] | | VR1[kΩ] | Vref_co2_a | Vref_co2_b | Vref_co2_c | Vref_co2_d |
| | Temp_L | Temp_H | | | | | |
| --- | --- | --- | --- | --- | --- | --- | --- |
| 1 | 0 | 35 | 27.0 | 2.3817E−06 | −0.000179 | 0.002233 | −0.182027 |
| 2 | 35 | 45 | 24.0 | −2.0288E−06 | 0.000327 | −0.018113 | −0.267364 |
| 3 | 45 | 50 | 20.0 | −1.9136E−05 | 0.002793 | −0.136470 | 1.177914 |
| 4 | 50 | 55 | 15.0 | 8.1265E−06 | −0.001205 | 0.059360 | −2.665517 |
| 5 | 55 | 60 | 10.0 | 4.0940E−06 | −0.000605 | 0.029830 | −2.188647 |

FIG. 3

GAS SENSOR

CROSS-REFERENCE TO RELATED APPLICATION

This application claims the benefit of Japanese Patent Application No. 2022-178048, filed on Nov. 7, 2022, the entire disclosure of which is incorporated by reference herein.

BACKGROUND OF THE ART

Field of the Art

The present disclosure relates to a gas sensor.

Description of Related Art

JP 2019-060848A discloses a gas sensor that calculates the concentration of gas to be measured based on the level of a signal appearing at the connection point between two series-connected thermistors. In the gas sensor described in JP 2019-060848A, a correction resistor is connected in parallel to one of the thermistors to cancel a measurement error caused due to gas not to be measured.

However, the present inventors have found that the influence that gas not to be measured has on a measurement result changes depending on environmental temperature.

SUMMARY

It is desirable to provide a gas sensor capable of cancelling the influence that gas not to be measured has on a measurement result more correctly.

A gas sensor according to the present disclosure includes a gas sensor part including first and second thermistors connected in series, a temperature sensor part configured to generate a temperature detection signal, a variable resistor connected in parallel to the first thermistor, and a control circuit configured to change a resistance value of the variable resistor based on the temperature detection signal.

BRIEF DESCRIPTION OF THE DRAWINGS

The above features and advantages of the present disclosure will be more apparent from the following description of certain preferred embodiments taken in conjunction with the accompanying drawings, in which:

FIG. 3 is a diagram showing an example of the data table 26;

DETAILED DESCRIPTION OF THE EMBODIMENTS

Preferred embodiments of the present disclosure will be explained below in detail with reference to the accompanying drawings.

Figure 1:
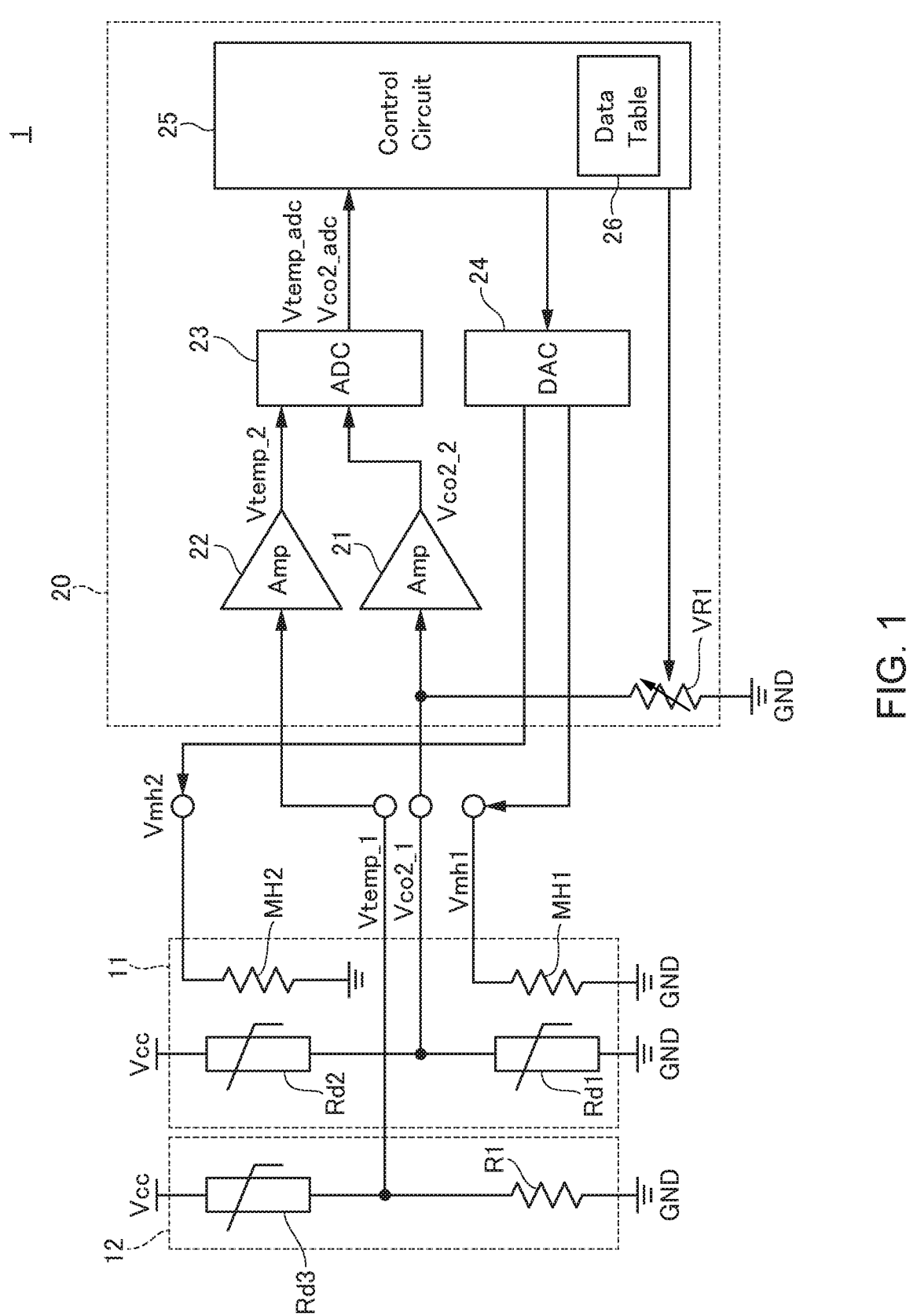
FIG. 1 is a circuit diagram illustrating the configuration of a gas sensor 1 according to one embodiment of technology according to the present disclosure.

FIG. 1 is a circuit diagram illustrating the configuration of a gas sensor 1 according to one embodiment of technology according to the present disclosure.

As illustrated in FIG. 1, the gas sensor 1 according to the present embodiment has a gas sensor part 11, a temperature sensor part 12, and a signal processing circuit 20. Although not particularly limited, the gas sensor 1 according to the present embodiment is configured to detect the concentration of $CO_2$ gas in the atmosphere.

The gas sensor part 11 is constituted by a heat conduction type gas sensor for measuring the concentration of $CO_2$ gas which is gas to be measured and includes series-connected thermistors Rd1 and Rd2 and heater resistors MH1 and MH2 for heating the thermistors Rd1 and Rd2, respectively. The temperature sensor part 12 includes a thermistor Rd3 and a fixed resistor R1 which are connected in series to each other. The thermistors Rd1 to Rd3 are each a detection element made of a material having a negative resistance temperature coefficient, such as a composite metal oxide, amorphous silicon, polysilicon, or germanium. The thermistors Rd1 and Rd2 are both configured to detect the concentration of $CO_2$ gas but have mutually different operating temperatures as described later. The thermistor Rd3 functions as a temperature sensor for detecting environmental temperature.

As illustrated in FIG. 1, the thermistors Rd1 and Rd2 are connected in series between a wire supplied with a power supply potential Vcc and a wire supplied with a ground potential GND. The thermistor Rd1 is heated to, for example, 300° C. by the heater resistor MH1, and the thermistor Rd2 is heated to, for example, 150° C. by the heater resistor MH2. The thermistor Rd1 is designed to have a predetermined resistance value when heated to 300° C., and the thermistor Rd2 is designed to have a predetermined resistance value when heated to 150° C. A gas detection signal Vco2_1 appears at the connection point between the thermistors Rd1 and Rd2.

When $CO_2$ gas is present in the measuring atmosphere in a state where the thermistor Rd2 as a detection element is heated to 150° C., the heat dissipation characteristics of the thermistor Rd2 change in accordance with the concentration of $CO_2$ gas. This change appears as a change in the resistance value of the thermistor Rd2. On the other hand, when $CO_2$ gas is present in the measuring atmosphere in a state where the thermistor Rd1 as a reference element is heated to 300° C., the heat dissipation characteristics of the thermistor Rd1 hardly change in accordance with $CO_2$ gas concentration. Accordingly, a change in the resistance value of the thermistor Rd1 heated to 300° C. in accordance with $CO_2$ gas concentration is sufficiently smaller than a change in the resistance value of the thermistor Rd2 heated to 150° C. in accordance with $CO_2$ gas concentration and may be imperceptible. The gas detection signal Vco2_1 appearing at the connection point between the thermistors Rd1 and Rd2 is supplied to the signal processing circuit 20.

When steam is present in the measurement atmosphere in a state where the thermistors Rd1 and Rd2 are heated, the heat dissipation characteristics of the thermistors Rd1 and Rd2 change in accordance with the concentration of steam. A change in the resistance value of the thermistor Rd1 heated to 300° C. due to humidity is larger than a change in the resistance value of the thermistor Rd2 heated to 150° C.

due to humidity. The difference in sensitivity with respect to humidity between the thermistors Rd1 and Rd2 changes also depending on environmental temperature, and the higher environmental temperature is, the larger the difference in sensitivity with respect to humidity between the thermistors Rd1 and Rd2 becomes. The difference in sensitivity with respect to humidity between the thermistors Rd1 and Rd2 is canceled by a variable resistor VR1 connected in parallel to the thermistor Rd1.

The thermistor Rd3 and the fixed resistor R1 are connected in series between a wire supplied with a power supply potential Vcc and a wire supplied with a ground potential GND. A temperature detection signal Vtemp_1 appears at the connection point between the fixed resistor R1 and the thermistor Rd3. The temperature detection signal Vtemp_1 is input to the signal processing circuit 20.

The signal processing circuit 20 has amplifiers 21 and 22, an AD converter (ADC) 23, a DA converter (DAC) 24, and a control circuit 25. The amplifier 21 amplifies the gas detection signal Vco2_1 to generate a gas detection signal Vco2_2. The amplifier 22 amplifies the temperature detection signal Vtemp_1 to generate a temperature detection signal Vtemp_2. The gas detection signal Vco2_2 and temperature detection signal Vtemp_2 are input to the AD converter 23. The AD converter 23 AD-converts the gas detection signal Vco2_2 and temperature detection signal Vtemp_2 to generate a digital gas detection value Vco2_adc and a digital temperature detection value Vtemp_adc. The digital gas detection value Vco2_adc and digital temperature detection value Vtemp_adc are supplied to the control circuit 25.

The control circuit 25 has a data table 26. As described above, the control circuit 25 performs calculation based on the temperature detection value Vtemp_adc to calculate environmental temperature and selects a predetermined table in the data table 26 in accordance with the calculated environmental temperature to change the resistance value of the variable resistor VR1. Further, the control circuit 25 performs calculation based on the gas detection value Vco2_adc to generate an output signal OUT indicating the concentration of $CO_2$ gas. On the other hand, the DA converter 24 DA-converts the digital values supplied from the control circuit 25 to generate heater voltages Vmh1 and Vmh2. The heater voltages Vmh1 and Vmh2 are applied to the heater resistors MH1 and MH2, respectively, to thereby heat the thermistors Rd1 and Rd2.

The variable resistor VR1 may be included in or provided outside the signal processing circuit 20. Alternatively, the variable resistor VR1 may be included in the gas sensor part 11.

The following describes an operation performed by the control circuit 25.

Figure 2:
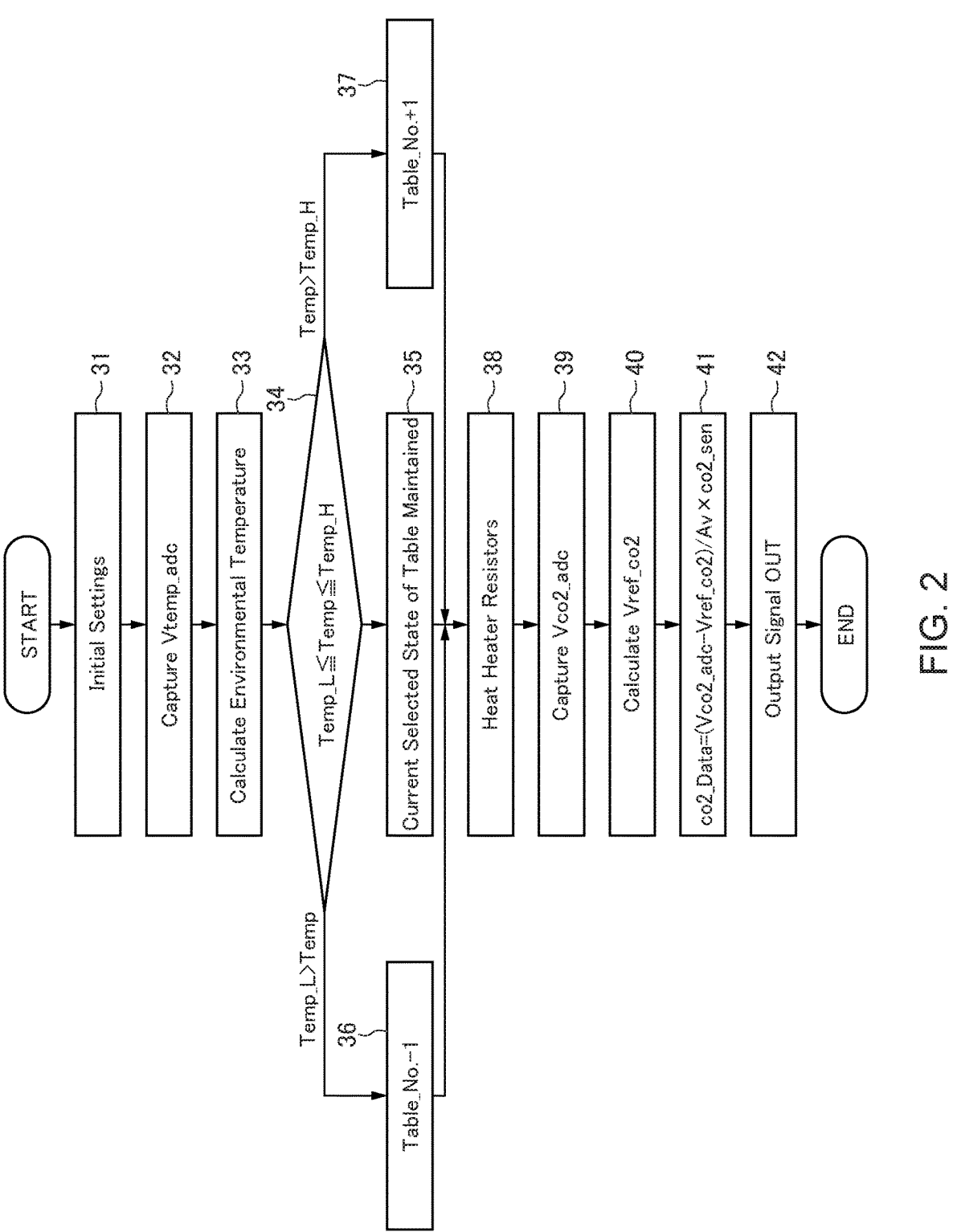
FIG. 2 is a flowchart for explaining an operation performed by the control circuit 25.

FIG. 2 is a flowchart for explaining an operation performed by the control circuit 25.

The control circuit 25 starts operation and performs various initial settings such as temporary selection of the data table 26 (step 31). After that, the control circuit 25 takes in the temperature detection value Vtemp_adc (step 32) and calculates environmental temperature based on the calculated temperature detection value Vtemp_adc (step 33). The calculation of the environmental temperature Temp can be made using the following formula (1). In the formula (1), "B" is the B constant of the thermistor Rd3, and "Vtemp_adc@25" is the temperature detection value Vtemp_adc obtained when environmental temperature is 25° C.

$$Temp = \frac{B}{\log_e \left( (Vcc - Vtemp_{adc}) \times \frac{R1}{Vtemp_{adc}} \right) - \log_e \left( (Vcc - Vtemp_{adc}) \times \frac{R1}{Vtemp_{adc}@25} \right) + \frac{B}{273.15}} \tag{1}$$

Then, the control circuit 25 refers to the data table 26 to determine within which range the calculated environmental temperature Temp lies (step 34). An example of the data table 26 is shown in FIG. 3. The data table 26 shown in FIG. 3 includes tables No. 1 to No. 5 in which mutually different temperature ranges are set. When the current environmental temperature is included in the temperature range corresponding to a table that has been temporarily selected in the initial setting, the current selection state of the table is maintained (step 35). On the other hand, when the current environmental temperature falls outside the temperature range corresponding to a table that has been temporarily selected in the initial setting, the selection state of the table is changed. In this case, when the current environmental temperature is lower than the temperature range corresponding to a table that has been temporarily selected in the initial setting, the table No. is decremented by one (step 36), while when the current environmental temperature is higher than the temperature range corresponding to a table that has been temporarily selected in the initial setting, the table No. is incremented by one (step 37). Alternatively, it may be possible to directly select a table corresponding to the current environmental temperature without performing temporary selection of the data table 26 in the initial setting.

Figure 4:
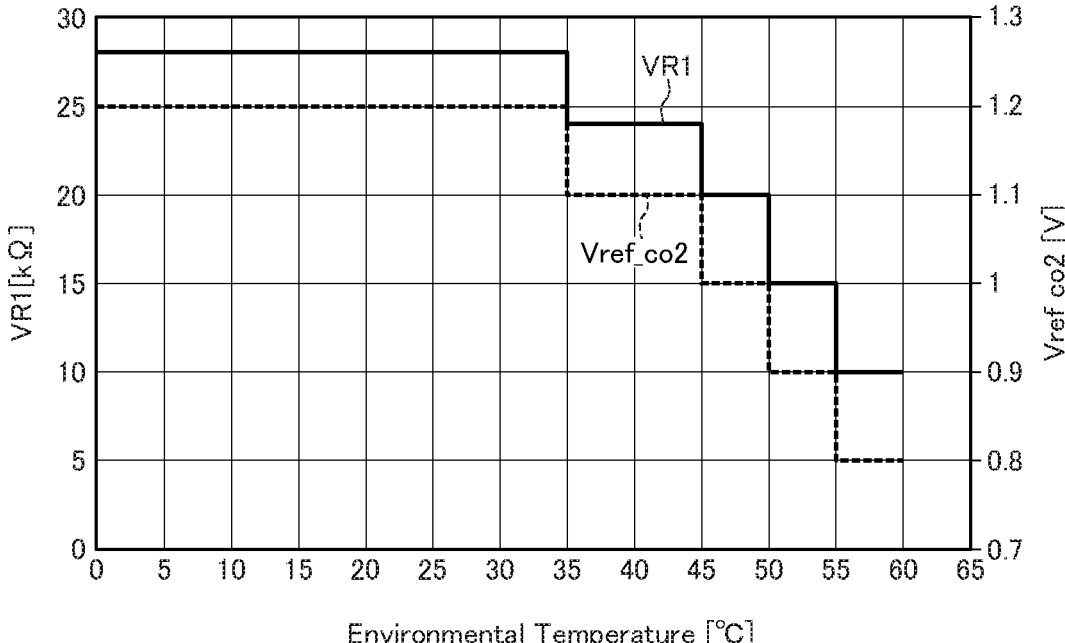
FIG. 4 is a graph showing changes in the resistance value of the variable resistor VR1 and the reference value Vref_co2 according to the environmental temperature.

As shown in FIG. 3, each of the tables of the data table 26 is assigned with its corresponding resistance value of the variable resistor VR1. The resistance value of the variable resistor VR1 is set to decrease as the table No. becomes larger, that is, as environmental temperature becomes higher. Thus, as illustrated in FIG. 4, the resistance value decreases stepwise as environmental temperature becomes higher.

Then, the heater voltages Vmh1 and Vmh2 are generated to heat the heater resistors MH1 and MH2 (step 38). The levels of the heater voltages Vmh1 and Vmh2 may be finely adjusted in accordance with the calculated environmental temperature Temp so as to heat the thermistors Rd1 and Rd2 to 300° C. and 150° C., respectively. Then, in this state, the control circuit 25 takes in the gas detection value Vco2_adc (step 39) and calculates a reference value Vref_co2 (step 40). The reference value Vref_co2 corresponds to a level obtained as a result of AD-conversion of the gas detection signal Vco2_2 when the concentration of the gas to be measured indicates a value normally obtained in normal time. In other words, the value of the gas detection value Vco2_adc to be originally input to the control circuit 25 when the concentration of the gas to be measured indicates a value normally obtained in normal time is the reference value Vref_co2. In the present embodiment, the gas to be measured is $CO_2$ gas, and the concentration of $CO_2$ gas in the atmosphere is about 400 ppm. The concentration of $CO_2$ gas in the atmosphere differs from one observation location to another, so that the concentration value in normal time refers to the concentration of $CO_2$ gas in the atmosphere at a location where observation is made. Further, in normal time, $CO_2$ gas concentration in the indoor environment is sometimes higher than that in the outdoor environment; in this case, $CO_2$ gas concentration in a sufficiently ventilated state is defined as the concentration in normal time.

The reference value Vref_co2 can be calculated according to the following formula (2). In the formula (2), "Vref_co2_a", "Vref_co2_b", "Vref_co2_c", and "Vref_co2_d" are coefficients assigned to each of the tables of the data table 26 shown in FIG. 3.

$$Vref\_co2 = Vref\_co2\_a \times Temp^3 + Vref\_Temp^2 + Vref\_co2\_c \times Temp + Vref\_co2\_d \quad (2)$$

Thus, in the present embodiment, not only the resistance value of the variable resistor VR1, but also a constant in the calculation formula used for calculating the reference value Vref_co2 changes in accordance with environmental temperature. As a result, as illustrated in FIG. 4, as environmental temperature becomes higher, the value of the reference value Vref_co2 to be calculated decreases stepwise with a reduction in the resistance value of the variable resistor VR1. The reason why the value of the reference value Vref_co2 is thus reduced stepwise with a reduction in the resistance value of the variable resistor VR1 is to compensate for a reduction in a midpoint potential appearing at the connection point between the thermistors Rd1 and Rd2 due to the reduction in the resistance value of the variable resistor VR1. Further, the above formula (2) includes the environmental temperature Temp, allowing a correct value to be obtained as the reference value Vref_co2 in accordance with the environment temperature Temp.

Then, the control circuit 25 calculates a gas concentration value $CO_2$ Data based on a difference value between the gas detection value Vco2_adc and the reference value Vref_co2, a gain Av of the amplifier 21, and a sensitivity coefficient CO2_sen (step 41) and outputs the calculated gas concentration value CO2_Data as the output signal OUT (step 42).

As described above, in the gas sensor 1 according to the present embodiment, the resistance value of the variable resistor VR1 is changed in accordance with environmental temperature, and the calculation formula used for calculating the reference value Vref_co2 is also changed in accordance with environmental temperature. Thus, even when the difference in sensitivity with respect to humidity between the thermistors Rd1 and Rd2 changes in accordance with environmental temperature, $CO_2$ gas concentration can be measured correctly. In addition, switching of the resistance value of the variable resistor VR1 and change in the calculation formula used for calculating the reference value Vref_co2 are performed stepwise, facilitating control by the control circuit 25.

Figure 5:
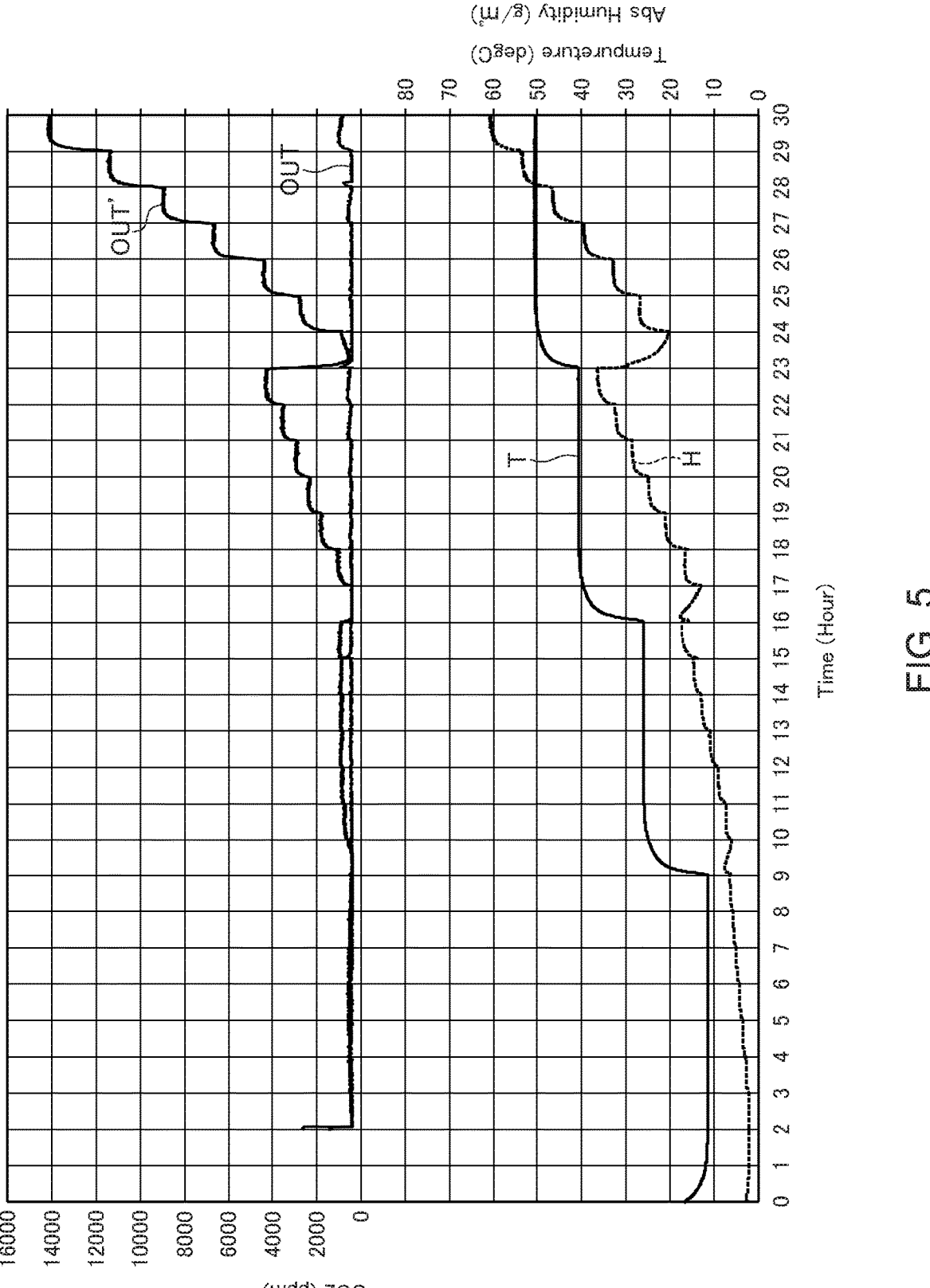
FIG. 5 is a graph illustrating actual measurement values for explaining effects of the gas sensor 1.

FIG. 5 is a graph illustrating actual measurement values for explaining effects of the gas sensor 1 according to the present embodiment. In FIG. 5, a symbol OUT denotes an output signal of the gas sensor 1 according to the present embodiment, and a symbol OUT' denotes an output signal of a conventional gas sensor. A symbol T denotes environment temperature, and a symbol H denotes the absolute humidity. The horizontal axis in FIG. 5 represents time, and the vertical axis represents $CO_2$ gas concentration, temperature, or humidity.

The graph of FIG. 5 reveals the following: in the conventional gas sensor, even when $CO_2$ gas concentration in the atmosphere is constant at 400 ppm, an increase in environmental temperature increases a measurement error due to humidity; while in the gas sensor 1 according to the present embodiment, a correct $CO_2$ gas concentration value can be output irrespective of environmental temperature and humidity.

Figure 6:
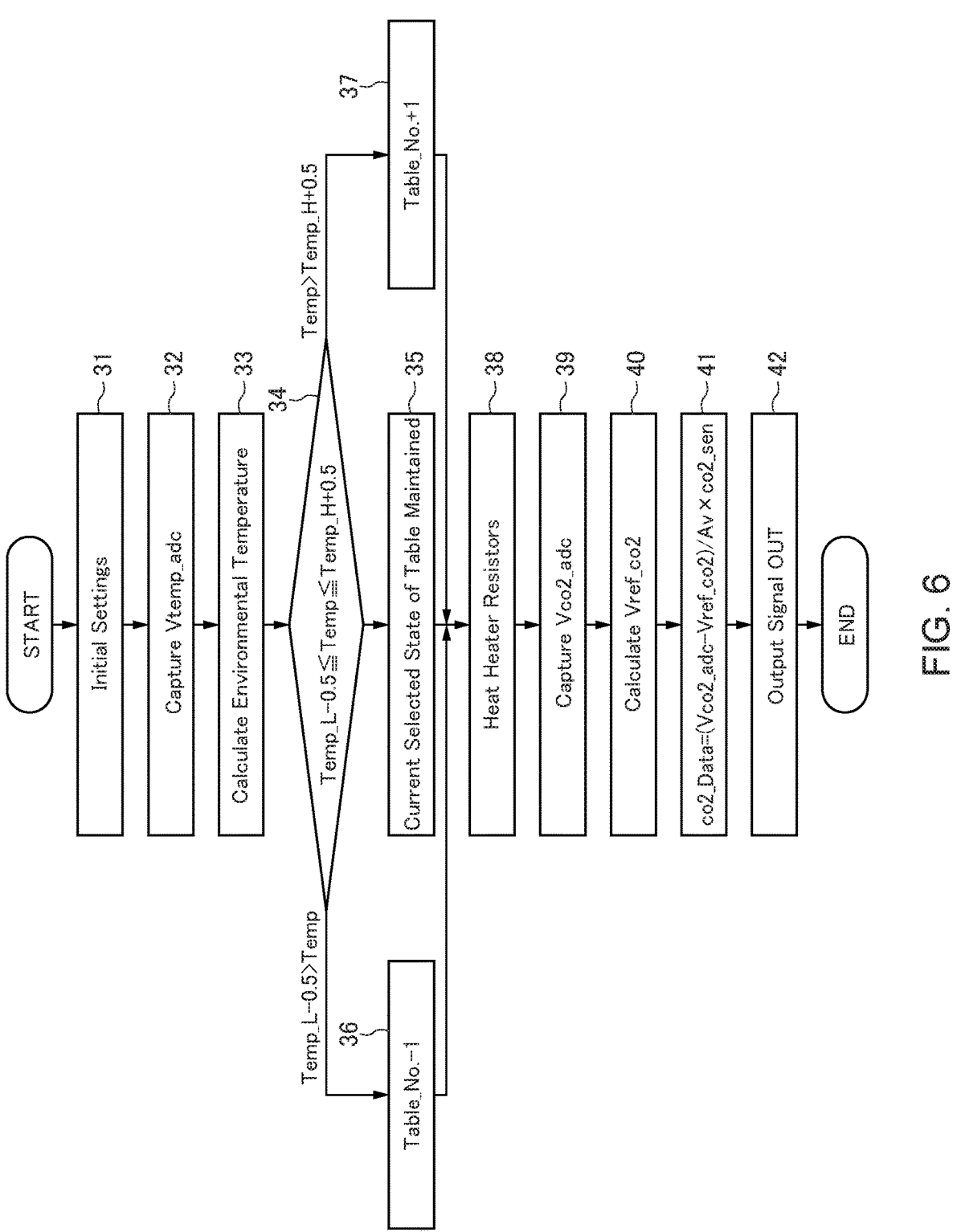
FIG. 6 is a flowchart for explaining an operation according to a modification performed by the control circuit 25.

FIG. 6 is a flowchart for explaining an operation according to a modification performed by the control circuit 25.

The operation according to a modification illustrated in FIG. 6 differs from the operation illustrated in FIG. 2 in that the temperature range assigned to each table is widened by 0.5° C. to the upper and lower temperature sides. That is, the lower limit value of the temperature range is set to a value lower than that of the temperature range assigned to each table by 0.5° C., and when the current temperature range falls below this lower limit value, the processing step proceeds to step 36. Similarly, the upper limit value of the temperature range is set to a value higher than that of the temperature range assigned to each table by 0.5° C., and when the current temperature range exceeds this upper limit value, the processing step proceeds to step 37.

Figure 7:
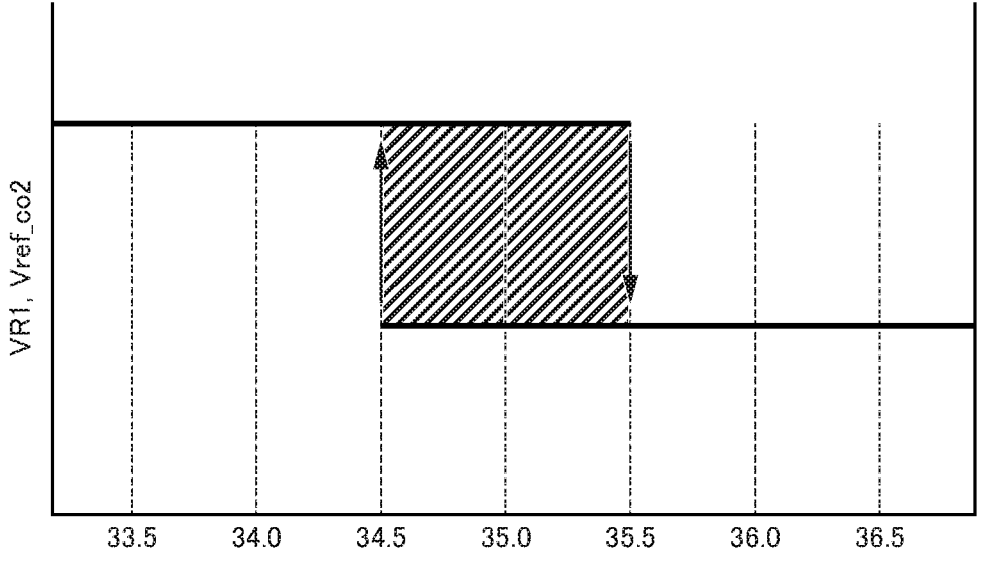
FIG. 7 is a waveform diagram for explaining the transition between Table No. 1 and Table No. 2.

Thus, as illustrated in FIG. 7, the condition for causing transition from the table No. 1 to table No. 2 due to, for example, an increase in environmental temperature is that environmental temperature exceeds 35.5° C., and the condition for causing transition from the table No. 2 to table No. 1 due to a reduction in environmental temperature is that environmental temperature falls below 34.5° C. As described above, imparting hysteresis to the table transition makes so-called chattering unlikely to occur, allowing more stable control to be performed.

While the preferred embodiment of the present disclosure has been described, the present disclosure is not limited to the above embodiment, and various modifications may be made within the scope of the present disclosure, and all such modifications are included in the present disclosure.

For example, in the above embodiment, although $CO_2$ gas is the gas to be measured, and steam is gas not to be measured acting as noise, the present invention is not limited to this. Further, the sensor part used in the present invention need not necessarily be a heat conduction type sensor and may be a sensor of another type such as a contact combustion type. For example, when CO gas is the gas to be measured, a sensor part of a contact combustion type can be used.

Further, in the above embodiment, the resistance value of the variable resistor VR1 is reduced as environmental temperature becomes higher; however, when the difference in sensitivity with respect to the gas not to be measured between the thermistors Rd1 and Rd2 becomes larger as environmental temperature becomes lower, the resistance value of the variable resistor VR1 may be reduced as environmental temperature becomes lower. Further, in the above embodiment, the variable resistor VR1 is connected in parallel to the thermistor Rd1; however, when a change in the resistance value of the thermistor Rd2 due to the concentration of the gas not to be measured is larger than a change in the resistance value of the thermistor Rd1 due to the concentration of the gas not to be measured, the variable resistor VR1 may be connected in parallel to the thermistor Rd2.

The technology according to the present disclosure includes the following configuration examples but not limited thereto.

A gas sensor according to the present disclosure includes a gas sensor part including series-connected first and second thermistors, a temperature sensor part that generates a temperature detection signal, a variable resistor connected in parallel to the first thermistor, and a control circuit. The control circuit changes the resistance value of the variable resistor based on the temperature detection signal. This can cancel the influence that the gas not to be measured has on a measurement result more correctly.

In the above gas sensor, the first thermistor may be heated to a first temperature by a first heater, the second thermistor may be heated to a second temperature different from the first temperature by a second heater, the sensitivity of the first thermistor heated to the first temperature with respect to the gas to be measured may be lower than the sensitivity of the second thermistor heated to the second temperature with respect to the gas to be measured, and the sensitivity of the first thermistor heated to the first temperature with respect to the gas not to be measured may be higher than the sensitivity of the second thermistor heated to the second temperature with respect to the gas not to be measured. This allows a measurement error due to the difference in sensitivity with respect to the gas not to be measured between the first and second thermistors to be cancelled by the variable resistor.

In the above gas sensor, the control circuit may reduce the resistance value of the variable resistor as a temperature value indicated by the temperature detection signal increases. Thus, even when the difference in sensitivity with respect to the gas not to be measured between the first and second thermistors becomes larger as environmental temperature becomes higher, a measurement error caused thereby can be cancelled by the variable resistor.

In the above gas sensor, the control circuit may change stepwise the resistance value of the variable resistor based on the temperature detection signal. This allows a measurement error to be cancelled by simple control.

In the above gas sensor, the control circuit may make mutually different the level of the temperature detection signal serving as a reference for changing the resistance value of the variable resistor from a first resistance value to a second resistance value when the temperature detection signal indicates an increase in temperature and the level of the temperature detection signal serving as a reference for changing the resistance value of the variable resistor from the second resistance value to the first resistance value when the temperature detection signal indicates a reduction in temperature. This makes so-called chattering unlikely to occur.

In the above gas sensor, the control circuit may generate an output signal indicating the concentration of the gas to be measured based on a gas detection signal appearing at the connection point between the first and second thermistors and may compare a gas detection value based on the gas detection signal with a reference value corresponding to the level of the gas detection signal normally obtained when the concentration of the gas to be measured indicates a concentration value in normal time to generate the output signal, and the control circuit may change stepwise the reference value with a stepwise change in the resistance value of the variable resistor. This allows the reference value to follow a change in a midpoint potential between the first and second thermistors due to a change in the resistance value of the variable resistor.

What is claimed is:

1. A gas sensor comprising:
   a gas sensor part including first and second thermistors connected in series;
   a temperature sensor part configured to generate a temperature detection signal;
   a variable resistor connected in parallel to the first thermistor; and
   a control circuit configured to change a resistance value of the variable resistor based on the temperature detection signal,
   wherein the control circuit is configured to reduce the resistance value of the variable resistor as a temperature value indicated by the temperature detection signal increases.

2. The gas sensor as claimed in claim 1,
   wherein the first thermistor is heated to a first temperature by a first heater,
   wherein the second thermistor is heated to a second temperature different from the first temperature by a second heater,
   wherein a sensitivity of the first thermistor heated to the first temperature with respect to a gas to be measured is lower than a sensitivity of the second thermistor heated to the second temperature with respect to the gas to be measured, and
   wherein a sensitivity of the first thermistor heated to the first temperature with respect to a gas not to be measured is higher than a sensitivity of the second thermistor heated to the second temperature with respect to the gas not to be measured.

3. A gas sensor comprising:
   a gas sensor part including first and second thermistors connected in series;
   a temperature sensor part configured to generate a temperature detection signal;
   a variable resistor connected in parallel to the first thermistor; and
   a control circuit configured to change stepwise a resistance value of the variable resistor based on the temperature detection signal,
   wherein the control circuit is configured to change the resistance value of the variable resistor from a first resistance value to a second resistance value when the temperature detection signal exceeds a first level, and
   wherein the control circuit is configured to change the resistance value of the variable resistor from the second resistance value to the first resistance value when the temperature detection signal falls below a second level different from the first level.

4. The gas sensor as claimed in claim 3,
   wherein the first thermistor is heated to a first temperature by a first heater,
   wherein the second thermistor is heated to a second temperature different from the first temperature by a second heater,
   wherein a sensitivity of the first thermistor heated to the first temperature with respect to a gas to be measured is lower than a sensitivity of the second thermistor heated to the second temperature with respect to the gas to be measured, and
   wherein a sensitivity of the first thermistor heated to the first temperature with respect to a gas not to be measured is higher than a sensitivity of the second thermistor heated to the second temperature with respect to the gas not to be measured.

5. The gas sensor as claimed in claim 3, wherein the control circuit is configured to:
   generate an output signal indicating a concentration of a gas to be measured based on a gas detection signal appearing at a connection point between the first and second thermistors;
   compare a gas detection value based on the gas detection signal with a reference value corresponding to a level of the gas detection signal normally obtained when a concentration of the gas to be measured indicates a concentration value in normal time to generate the output signal; and
   change stepwise the reference value with a stepwise change in the resistance value of the variable resistor.

6. A gas sensor comprising:

a gas sensor part including first and second thermistors connected in series;

a temperature sensor part configured to generate a temperature detection signal;

a variable resistor connected in parallel to the first thermistor; and a control circuit configured to change stepwise a resistance value of the variable resistor based on the temperature detection signal, wherein the control circuit is configured to:

generate an output signal indicating a concentration of a gas to be measured based on a gas detection signal appearing at a connection point between the first and second thermistors;

compare a gas detection value based on the gas detection signal with a reference value corresponding to a level of the gas detection signal normally obtained when a concentration of the gas to be measured indicates a concentration value in normal time to generate the output signal; and change stepwise the reference value with a stepwise change in the resistance value of the variable resistor.

7. The gas sensor as claimed in claim 6, wherein the first thermistor is heated to a first temperature by a first heater, wherein the second thermistor is heated to a second temperature different from the first temperature by a second heater, wherein a sensitivity of the first thermistor heated to the first temperature with respect to a gas to be measured is lower than a sensitivity of the second thermistor heated to the second temperature with respect to the gas to be measured, and wherein a sensitivity of the first thermistor heated to the first temperature with respect to a gas not to be measured is higher than a sensitivity of the second thermistor heated to the second temperature with respect to the gas not to be measured.

8. A gas sensor comprising:

a gas sensor part including first and second thermistors connected in series;

a temperature sensor part configured to generate a temperature detection signal;

a variable resistor connected in parallel to the first thermistor; and a control circuit configured to change a resistance value of the variable resistor based on the temperature detection signal, wherein the control circuit is configured to reduce stepwise the resistance value of the variable resistor as a temperature value indicated by the temperature detection signal increases.

9. The gas sensor as claimed in claim 8, wherein the first thermistor is heated to a first temperature by a first heater, wherein the second thermistor is heated to a second temperature different from the first temperature by a second heater, wherein a sensitivity of the first thermistor heated to the first temperature with respect to a gas to be measured is lower than a sensitivity of the second thermistor heated to the second temperature with respect to the gas to be measured, and wherein a sensitivity of the first thermistor heated to the first temperature with respect to a gas not to be measured is higher than a sensitivity of the second thermistor heated to the second temperature with respect to the gas not to be measured.

10. The gas sensor as claimed in claim 8, wherein the control circuit is configured to change the resistance value of the variable resistor from a first resistance value to a second resistance value when the temperature detection signal exceeds a first level, and wherein the control circuit is configured to change the resistance value of the variable resistor from the second resistance value to the first resistance value when the temperature detection signal falls below a second level different from the first level.

11. The gas sensor as claimed in claim 8, wherein the control circuit is configured to:

generate an output signal indicating a concentration of a gas to be measured based on a gas detection signal appearing at a connection point between the first and second thermistors;

compare a gas detection value based on the gas detection signal with a reference value corresponding to a level of the gas detection signal normally obtained when a concentration of the gas to be measured indicates a concentration value in normal time to generate the output signal; and change stepwise the reference value with a stepwise change in the resistance value of the variable resistor.

* * * * *